US009616009B2

United States Patent
Baudouin et al.

(10) Patent No.: US 9,616,009 B2
(45) Date of Patent: *Apr. 11, 2017

(54) COMPOSITION CONTAINING AT LEAST ONE C7 SUGAR FOR ALOPECIA TREATMENT, COSMETIC TREATMENT OF HAIR AND NAILS, AND CARE OF HAIR, EYELASHES OR NAILS

(71) Applicant: LABORATOIRES EXPANSCIENCE, Courbevoie (FR)

(72) Inventors: Caroline Baudouin, Rambouillet (FR); Philippe Msika, Versailles (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/514,646

(22) Filed: Oct. 15, 2014

(65) Prior Publication Data

US 2015/0030550 A1    Jan. 29, 2015

Related U.S. Application Data

(63) Continuation of application No. 13/516,333, filed as application No. PCT/EP2010/069806 on Dec. 15, 2010, now Pat. No. 8,894,979.

(30) Foreign Application Priority Data

Dec. 16, 2009 (FR) ..................... 09 59075

(51) Int. Cl.
| A61K 8/60 | (2006.01) |
| A61K 8/97 | (2017.01) |
| A61K 9/48 | (2006.01) |
| A61K 31/70 | (2006.01) |
| A61K 31/7004 | (2006.01) |
| A61K 36/54 | (2006.01) |
| A61K 45/06 | (2006.01) |
| A61Q 3/00 | (2006.01) |
| A61Q 7/00 | (2006.01) |
| A23L 2/52 | (2006.01) |
| A61Q 5/02 | (2006.01) |
| A61Q 5/06 | (2006.01) |
| A61Q 5/12 | (2006.01) |
| A23L 7/126 | (2016.01) |
| A61Q 5/00 | (2006.01) |

(52) U.S. Cl.
CPC  *A61K 8/60* (2013.01); *A23L 2/52* (2013.01); *A23L 7/126* (2016.08); *A61K 8/97* (2013.01); *A61K 9/4858* (2013.01); *A61K 31/70* (2013.01); *A61K 31/7004* (2013.01); *A61K 36/54* (2013.01); *A61K 45/06* (2013.01); *A61Q 3/00* (2013.01); *A61Q 5/006* (2013.01); *A61Q 5/02* (2013.01); *A61Q 5/06* (2013.01); *A61Q 5/12* (2013.01); *A61Q 7/00* (2013.01); *A23V 2002/00* (2013.01); *A61K 2800/5922* (2013.01); *A61K 2800/92* (2013.01); *A61Q 5/00* (2013.01)

(58) Field of Classification Search
CPC . A61K 31/70; A61K 8/60; A61K 8/97; A61K 9/4858; A61Q 7/00
See application file for complete search history.

(56) References Cited

U.S. PATENT DOCUMENTS

| 4,139,619 | A | 2/1979 | Chidsey, III |
| 4,596,812 | A | 6/1986 | Chidsey, III et al. |
| 4,849,214 | A * | 7/1989 | Ruiseco ............ A61K 8/922 424/705 |
| 6,030,948 | A * | 2/2000 | Mann ............... A61K 8/41 514/20.7 |
| 7,897,579 | B2 | 3/2011 | Piccirilli et al. |
| 8,318,186 | B2 | 11/2012 | Msika et al. |
| 2003/0092669 | A1 | 5/2003 | Chapnick et al. |
| 2008/0113921 | A1* | 5/2008 | Piccirilli ............ A61K 8/60 514/23 |
| 2010/0136144 | A1* | 6/2010 | Msika ............... A23D 9/007 514/1.1 |

FOREIGN PATENT DOCUMENTS

| EP | 0 353 123 A1 | 1/1990 |
| EP | 0 420 707 B1 | 4/1991 |
| EP | 0 459 890 B1 | 12/1991 |
| EP | 0 519 819 B1 | 12/1992 |

(Continued)

OTHER PUBLICATIONS

Schroder, J-M.; Harder, J. "Human beta-defensin-2" Int J Biochem Cell B, 1999, 31, 645-651.*
Tesfay, S.Z.; Bertling, I.; Bower, J.P. "D-mannoheptulose and perseitol in 'Hass' avocado: Metabolism in seed and mesocarp tissue" South African Journal of Botany 2012, 79, 159-165.*
Mannoheptulose (https://www.caymanchem.com/pdfs/16548.pdf) 2014, p. 1.*
Dreher, M.L.; Davenport, A.J. "Hass Avocado Composition and Potential Health Effects" Critical Reviews in Food Science and Nutrition 2013, 53, 738-750.*
Liu et al. 'Hass' Avocado Carbohydrate Fluctuations. II. Fruit Growth and Ripening. J. Amer. Soc. Hort. Sci. 1999, 124(6), 676-681.*

(Continued)

*Primary Examiner* — Timothy Thomas
*Assistant Examiner* — Andrew S Rosenthal
(74) *Attorney, Agent, or Firm* — Foley & Lardner LLP

(57) ABSTRACT

The present invention relates to a composition including at least one C7 sugar, or derivative from esterification of said sugar, and a pharmaceutically acceptable carrier for treating alopecia. The present invention also relates to a method for cosmetically treating hair and nails, said method being intended to stimulate the growth thereof and/or slow the loss thereof. According to said method, a cosmetic composition including at least one C7 sugar, or derivative from esterification of said sugar, is administered. The present invention finally relates to a method for cosmetic care of hair and/or eyelashes and/or nails.

18 Claims, No Drawings

(56) References Cited

FOREIGN PATENT DOCUMENTS

| EP | 0 522 964 B1 | 1/1993 |
|---|---|---|
| EP | 0 408 442 B1 | 8/1994 |
| EP | 0 356 271 B1 | 4/1995 |
| FR | 2 843 027 A1 | 2/2004 |
| FR | 2 843 125 A1 | 2/2004 |
| WO | WO 95/03809 | 2/1995 |
| WO | WO 2004/000293 A2 | 12/2003 |
| WO | WO 2005/115421 A1 | 12/2005 |
| WO | WO 2008/025847 A2 | 3/2008 |

OTHER PUBLICATIONS

Liu et al. "Postulated physiological roles of the seven-carbon sugars, mannoheptulose, and perseitol in avocado" J. Amer. Soc. Hort. Sci. 2002, 127 (1), 108-114.*
Absorption and Effect of Ingested Mannoheptulose. Nutrition Reviews 1969, 27: 206-208.*
Gregoriou, S. et al. "Cytokines and OtherMediators in Alopecia Areata" Mediators of Inflammation 2010, 2010, pp. 1-6.*
Ito, T. et al. "The role of cytokines and chemokines in the T-cell-mediated autoimmune process in alopecia areata" Experimental Dermatology, 2014, 23, 787-791.*
Takenaga, F.; et al. Journal of Oleo Science 2008, 57 (11), 591-597.*
Lu, Y.; Chen, D-F. "Analysis of Schisandra chinensis and Schisandra sphenanthera" Journal of Chromatography A 2009, 1216, 1980-1990.*
Hoffman et al., Arch Dematol Res, vol. 288, 1996, pp. 153-156.*
Kwack et al., Society for Investigative Dermatology, vol. 132, 2012, pp. 43-49.*
Philpott et al., British Journal of Dermatology, vol. 135, 1996, pp. 942-948.*
Colquhoun, D.M.; Moores, D.; Somerset, S.M.; Humphries, J.A. "Comparison of the effects on lipoproteins and apolipoproteins of a diet high in monounsaturated fatty acids, enriched with avocado, and a high-carbohydrate diet" Am J Clin Nutr 1992, 56, 671-677.*
International Search Report issued in PCT/EP2010/069806, dated Feb. 22, 2011, 4 pages.
Paoletti et al., "Patented natural avocado sugars modulate the HBD-2 expression in human keratinocytes through the involvement of protein kinase C and protein tyrosine kinases," Arch. Dermatol. Res., 2010, pp. 201-209, vol. 302.
Shibuya et al., "Search for pharmacochemical leads from tropical rainforest plants," Pure Appl. Chem., 1999, pp. 1109-1113, vol. 71, No. 6.
Schroder, "Human beta-defensin-2," Int. J. Biochem Cell B, vol. 31, pp. 645-651, 1999.
Karleskind, ed., "Manuel des Corps Gras," Lavoisier, Oct. 2006.
Office Action issued in U.S. Appl. No. 13/516,333 on Mar. 7, 2013.
Office Action issued in U.S. Appl. No. 13/516,333 on Apr. 17, 2013.
Office Action issued in U.S. Appl. No. 13/516,333 on Sep. 24, 2013.
Office Action issued in U.S. Appl. No. 13/516,333 on Apr. 8, 2014.
Notice of Allowance issued in U.S. Appl. No. 13/516,333 on Jul. 25, 2014.
Hoffman et al., "Cytokines and growth factors influence hair growth in vitro. Possible implication for the pathogenesis and treatment of alopecia areata," Arch Dematol Res, vol. 288, 1996, pp. 153-156.
Kwack et al., "Dihydrotestosteron-Inducible IL-6 Inhibits Elongation of Human Hair Shafts by Suppressing Matrix Cell Proliferation and Promotes Regression of Hair Follicles in Mice," Society for Investigative Dermatology, vol. 132, 2012, pp. 43-49.
Philpott et al., "Effects of interleukins, colony-stimulating factor and tumour necrosis factor on human hair follicle growth in vitro: a possible role for interleukin-1 and tumour necrosis factor-α in alopecia areata," British Journal of Dermatology, vol. 135, 1996, pp. 942-948.

* cited by examiner

COMPOSITION CONTAINING AT LEAST ONE C7 SUGAR FOR ALOPECIA TREATMENT, COSMETIC TREATMENT OF HAIR AND NAILS, AND CARE OF HAIR, EYELASHES OR NAILS

This application is a continuation of U.S. patent application Ser. No. 13/516,333, filed Sep. 4, 2012, which is a U.S. National Stage of PCT/EP2010/069806, filed Dec. 15, 2010, which claims priority to French Application No. 0959075, filed Dec. 16, 2009, all of which are hereby incorporated by reference in their entirety.

The present invention relates to the use of C7 sugars in a composition for the care of hair and nails, intended to induce and/or stimulate the growth thereof and/or to slow the loss' thereof.

In particular, the invention relates to the use of C7 sugars to treat alopecia.

Hair growth and renewal are principally determined by the activity of hair follicles and their matrix environment.

Hair is alive and follows a natural growth cycle, sometimes referred to as the hair growth cycle. This cycle is divided into three phases: anagen, catagen and telogen.

The anagen phase is the growth phase of the hair, and is the longest part of the hair growth cycle since it lasts from two to five years. The very great majority of hairs are thus in anagen phase.

The catagen phase is a rest phase during which the hair ceases growing. It lasts approximately three weeks, which is quite short in relation to the preceding phase.

The telogen phase, finally, leads after about three months to the death and shedding of the hair, which will make room for a new follicle in anagen phase.

The number of hair growth cycles is limited: the hair goes through only 25 to 30 cycles during its entire life. Since these cycles last from two to five years; humans have quite enough hair growth cycles, theoretically, to maintain beautiful hair throughout their lives.

Unfortunately, for various reasons, including an inflammatory reaction exacerbated at the hair follicle, the duration of these cycles can decrease considerably and lead to total exhaustion of capillary potential in only a few years. The hair then starts by becoming increasingly thin, leading to baldness.

Hair loss is accompanied, as is now known, by inflammation at the root. Inflammation leads to the destruction of hair follicles and the development of scar tissue. Pro-inflammatory cytokines have shown to be capable of inhibiting in vitro the growth of isolated hair follicles placed in culture.

Alopecia is a loss of hair on all or part of the scalp. On average, 60 hairs per day are lost naturally. There are seasonal variations, with greater loss in the spring and autumn. However, a loss of more than 100 hairs per day is always excessive. Especially if it persists, the loss becomes abnormal and must be treated.

Alopecia affects roughly 20% of 20-year-old men and increases by roughly 10% every 10 years. In men, hair loss results in balding of gulfs and the top of the head. It is progressive and foreseeable. Slightly more than half of all men over 50 have some degree of baldness.

Although baldness is a primarily male phenomenon, alopecia also affects more and more women. In women, an overall decrease in hair is observed, predominantly on the top of the head.

The term alopecia also covers a whole family of attacks on the hair follicle, the eventual consequence of which is definitive, partial or general hair loss.

Diffuse hair loss can be distinguished from localized hair loss. Diffuse hair loss includes telogen effluvium, anagen effluvium, alopecia areata. Among causes of diffuse hair loss, the most frequent are common alopecia (male and female androgenic alopecia) and telogen effluvium (after a high fever, pregnancy, taking of medicine or a strict diet).

Localized hair loss includes androgenetic alopecia, alopecia areata, scarring alopecia and tumors. Localized hair loss is observed in the context of male androgenic alopecia (gulfs, tonsure), alopecia areata plaques, alopecia caused by pulling (trichotillomania, braids and straightening) or scarring alopecia (central centrifugal cicatricial alopecia, post-menopausal frontal fibrosing alopecia). Tumors and skin excrescences are also accompanied by localized hair loss (sebaceous hamartoma, basal-cell carcinoma, squamous-cell carcinoma).

It also appears that the presence of free radicals maintains tissue inflammation and promotes the aging of hair follicle cells. This inflammatory reaction is recognized as one of the causes of shorter hair life.

Generally, alopecia appears on the scalp but it can also appear on the entire body. On bald plaques, roots produce only thin hair that falls out rather quickly. The hair roots do not necessarily die following alopecia. If the inflammation disappears, the hair can start to grow again, sometimes after months, or even after years. Alopecia can also affect the nails.

The cosmetics and pharmaceutical industries have for many years sought compositions to eliminate or reduce alopecia, and notably to induce or stimulate growth of keratinous fibers, to include the hair, or to decrease their loss.

Accordingly, a large number of compositions containing highly diverse active agents have already been proposed, such as, for example, 2,4-diamino-6-piperidinopyrimidine 3-oxide (Minoxidil) described in the patents U.S. Pat. No. 4,139,619 and U.S. Pat. No. 4,596,812 or the many derivatives thereof such as those described, for example, in the patent applications EP0353123, EP0356271, EP0408442, EP0522964, EP0420707, EP0459890 and EP0519819.

The Applicant found in a surprising manner that the C7 sugars and derivatives of formula (I), which will be defined below, have, among others, anti-inflammatory activity with a beneficial effect on the protection of hair follicles and thus on the protection of the follicle after each growth cycle. These C7 sugars and derivatives are, surprisingly, endowed with activity favorable to increased hair and nail density. Thus, these compounds have a beneficial effect on the growth of human hair but also on the growth of eyelashes and certain human hairs as well as on the growth of nails.

D-mannoheptulose, the first ketoheptose identified in 1916 by La Forge, of general formula (II):

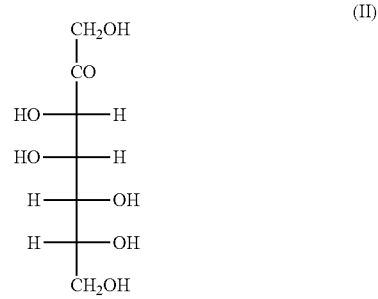

is found in certain plants, in particular in alfalfa (*Medicago sativa* L.), avocado, fig (*Ficus officinalis* L.) stonecrop (*Sedum spectabile* Bor.) and primula (*Primula officinalis* Jacq.). However, it is in avocado that the highest D-mannoheptulose content is found. D-mannoheptulose has already been used in therapeutic applications. For example, the patent application WO95/03809 describes the use of D-mannoheptulose, as a glucokinase inhibitor, to inhibit the development of tumor cells, and application US2003/0092669 describes an oral dietary supplement containing D-mannoheptulose, which decreases insulin levels and which thus enables weight loss.

Perseitol, a polyol form of D-mannoheptulose, of general formula (III):

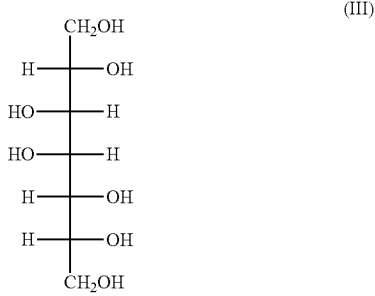

is also found in avocado, in particular in the fruit or the seed.

According to the publication "Search for pharmacochemical leads from tropical rainforest plants," Hitotaka Shibuya et al., Pure Appl. Chem., vol. 71, no. 6, pp 1109-1113, 1999, perseitol, associated with a potassium ion, inhibits the incorporation of 3H-leucine in tumor cells of Ehrlich's ascites carcinoma.

The use of these sugars (perseitol and D-mannoheptulose) to stimulate the synthesis of human beta-defensins (in particular HBD-2) has already been described (WO2005/115421). In particular, it was shown in this application that avocado sugars induce HBD-2 synthesis without inducing the synthesis of inflammatory mediators (which means that avocado sugars are incapable of stimulating the inflammatory reaction, but which does not make it possible to foresee what one anti-inflammatory action or other might be). The use of these sugars to treat candidiasis and seborrheic dermatitis has also already been described (WO2008/025847).

The invention relates to a composition containing at least one C7-sugar or derivative of the following formula (I):

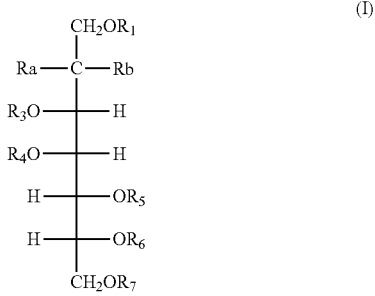

wherein:
Ra represents a hydrogen atom and Rb represents —OR$_2$ or CRaRb represents a CO radical;
R$_1$, R$_2$, R$_3$, R$_4$, R$_5$, R$_6$ and R$_7$ represent, independently of one another:
  a hydrogen atom or
  a —(CO)—R radical wherein R represents a saturated or unsaturated hydrocarbon chain containing from 11 to 24 carbon atoms, optionally substituted by one or more substituents selected from the group comprising hydroxy radicals (—OH), ethoxy radicals (—OC$_2$H$_5$) and an —SO$_3$M group with M representing a hydrogen atom, an ammonium ion (NH$_4^+$) or a metal ion; or
  a —(CO)—R' radical wherein R' represents a saturated or unsaturated hydrocarbon chain containing from 2 to 10 carbon atoms, optionally substituted by one or more substituents selected from the group comprising hydroxy radicals (—OH), ethoxy radicals (—OC$_2$H$_5$) and an —SO$_3$M group with M representing a hydrogen atom, an ammonium ion (NH$_4^+$) or a metal ion;
and a pharmaceutically acceptable excipient for the treatment of alopecia.

The term "alopecia" refers to both diffuse and localized hair loss. It covers in particular alopecia areata, diffuse hair loss, scarring alopecia, non-scarring alopecia and the disease of Quinquaud's disease.

Diffuse loss is characterized by thin and sparse hair over the entirety of the scalp. It is often due to external factors such as stress, high fever, fatigue, overwork, medications, dietary imbalances, effects of labor, significant surgical procedures, certain infectious diseases or tumors, pollution, etc. It is increasing quite rapidly, and affects between 20% and 40% of women.

Alopecia areata is characterized by alopecia plaques due to inflammation of the hair root, following a self-defense reaction of the immune system.

Scarring alopecia is characterized by hair loss due to an inflammatory disease of the skin (infection, inflammation, tumor, injury, burn, etc.) that permanently destroys the dermal papilla.

Non-scarring (non-cicatricial) alopecia is characterized by hair loss due to hair follicle dysfunction, which prematurely interrupts the growth phase.

Quinquaud's decalvans folliculitis (also known as Quinquaud's disease or Quinquaud's syndrome) is an orphan disease characterized by inflammation of follicles at the root of hair of the head and body. Inflammation of these follicles causes hair loss (alopecia), with the hair falling out in delimited areas (plaques). It is an extremely disabling and very painful disease.

The Applicant thus noted that the C7 sugars found in avocado, perseitol and mannoheptulose, as well as derivatives thereof from the esterification of one or more of the sugar's hydroxyl functional groups, advantageously with a fatty acid, are effective in the treatment of alopecia and stimulate the growth of hair and nails.

The expression "hair and nails" refers to the hair, eyelashes, eyebrows and nails, notably the hair and nails.

According to a first advantageous variant of the invention, the C7 sugars are in a free form (the hydroxyl functional groups are not esterified). The composition thus contains a C7 sugar selected from the group comprising mannoheptulose, perseitol and mixtures thereof.

The source of D-mannoheptulose and/or perseitol can be an avocado sugar water-soluble extract or sugars from another plant. Additionally, D-mannoheptulose and perseitol are available commercially (synthetic origin). According to an advantageous variant of the invention, the source of D-mannoheptulose and/or perseitol is an avocado sugar water-soluble extract.

The avocado sugar water-soluble extract can be obtained directly from any part of the avocado or avocado tree, such as the fruit, flesh or seed of the avocado or the leaves or roots of the avocado tree. It is also possible to obtain the avocado sugar water-soluble extract from the by-products of the avocado processing industry, including but in no way exhaustively: fresh avocado pulp, frozen pulp, dehydrated pulp, avocado oil cakes arising from oil extraction processes (mechanical extraction and/or by solvent using fruit dehydrated beforehand), de-oiled solid matter arising from wet oil extraction processes (centrifugation), de-oiled solid matter arising from enzymatic avocado oil extraction processes, crude mashed avocado (guacamole) and solid waste from units that manufacture such mashed avocado. The extract is advantageously obtained from the fresh fruit of the avocado tree. The fruits can be selected among the Hass, Fuerte, Ettinger, Bacon, Nabal, Anaheim, Lula, Reed, Zutano, Queen, Criola Selva, Mexicana Canta, Region Dschang, Hall, Booth, Peterson, and Collinson Redn varieties, more advantageously among the Hass, Fuerte and Reed varieties. Preferably, the Hass, Fuerte, Ettinger and Bacon varieties will be selected, and more advantageously the Hass and Fuerte varieties.

The fruit of the avocado tree is primarily composed of water, pulp, oil and seed. The proportions of these components are, like all natural and plant matter, highly variable. However, the mean composition data presented in Table 1 below, expressed in percentages of fresh fruit, are generally accepted:

TABLE 1

| | |
|---|---|
| Water | 70-85% |
| Proteins | 1.5-4.5% |
| Fats | 12-23% |
| Sugars | 1.5-5% |
| Fibers | 1.1-1.6% |

In fact, the avocado is not particularly polysaccharide-rich. However, the nature of soluble monosaccharides is quite specific, such as perseitol and D-mannoheptulose with 7 carbon atoms.

The avocado sugar water-soluble extract can be obtained by a method comprising the following successive steps:
    an avocado oil cake is obtained, advantageously from avocado fruit, through drying and extraction of the lipids (oil); after which
    total delipidation of said oil cake, then washing with water or with a hydroalcoholic medium and then decanting and centrifugation in order to recover a soluble fraction rich in C7 sugars (elimination of the cake);
    demineralization on ionic resin of said soluble fraction obtained in the preceding step; then
    ultrafiltration at 10,000 daltons; and
    as the case may be, concentration under vacuum and packaging.

The first step of the method consists in drying and then deoiling the fruit. Thus, after the fruit has been cut into thin slices, it may be dried by any of the techniques known to the person skilled in the art, among which mention may be made of hot air drying, lyophilization or osmotic drying. In general, the temperature during this drying step will be advantageously maintained at or below 80° C., regardless of the technique used. In the context of the present method, for reasons of ease of implementation and cost, drying in ventilated dryers, in thin layer and under a stream of hot air at a temperature between 70° C. and 75° C., is preferred. The duration of this operation can vary between 5 hours and 72 hours.

The lipids of the dried fruit are then extracted either mechanically in an expeller, or chemically with a solvent such as hexane in a Soxhlet extractor or in a De Smet® continuous belt extractor, notably according to the method described in the application FR2843027, or by a method using supercritical $CO_2$. Among the main advantages of the method, the oil by-product can quite clearly be recovered directly. For this reason mechanical lipid extraction is preferred. The dried and deoiled fruit, also called an oil cake, may then undergo the following steps:
    total delipidation, notably with acetone and/or ethanol,
    decanting and washing of the oil cake with water and/or a hydroalcoholic mixture,
    centrifugation, filtration and recovery of the soluble fraction (elimination of the oil cake),
    concentration,
    demineralization by ion exchange,
    ultrafiltration with a 10 kDa cutoff,
    concentration under vacuum, addition of preservative and packaging.

Generally, the final aqueous extract can contain by weight 0.1-20% dry matter, advantageously 1-10% dry matter, even more advantageously 3-5% dry matter. The content in C7 sugars, i.e., in D-mannoheptulose and perseitol, in the dry matter is advantageously between 50% and 100%, more particularly between 65% and 90% by weight, in relation to the total weight of the dry matter. The average analytical data for an aqueous solution with 5% dry extract, obtained by the method described above, are given in following Table 2:

TABLE 2

| | |
|---|---|
| pH (¼ dilution) | 3-5 |
| Absorbance 420 nm | Less than 0.200 |
| (½ dilution) 550 nm | Less than 0.050 |
| C7 sugars/dry matter | 50-100% |

The relative composition in sugars of the water-soluble extract, by weight in relation to the total weight of the dry matter of the extract, responds advantageously to the following criteria (relative composition determined by high-performance liquid chromatography (HPLC)):

| | |
|---|---|
| D-Mannoheptulose | 0-100%, in particular 5-80%, |
| Perseitol | 0-100%, in particular 5-80%, |
| Sucrose | less than 10%, |
| Glucose | less than 10%, |
| Fructose | less than 10%. |

The avocado sugar water-soluble extract contains advantageously, in relation to the total weight of the dry matter, 10-80% by weight D-mannoheptulose, more advantageously 15-70% by weight D-mannoheptulose. The avocado sugar water-soluble extract contains advantageously, in relation to the total weight of the dry matter, 20-80% by weight perseitol, more advantageously 25-70% by weight perseitol.

Preferably, the relative composition in sugars of the water-soluble extract, by weight in relation to the total weight of the dry matter of the extract, responds to the following criteria (relative composition determined by HPLC):

| | |
|---|---|
| D-Mannoheptulose | 25-60%, |
| Perseitol | 25-60%, |
| Sucrose | less than 10%, |
| Glucose | less than 10%, |
| Fructose | less than 10%. |

In a surprising manner, the Inventors noted a synergistic effect between D-mannoheptulose and/or perseitol and minority sugars (fructose, glucose, sucrose) present in the avocado sugar extract.

The extract obtained may be lyophilized in order to obtain a totally water-soluble solid power (dry extract).

Optionally, the extract obtained can be fractioned into each purified sugar. This separation and purification can be carried out by any of the techniques known to the person skilled in the art, among which mention may be made in a non-exhaustive manner of precipitation/filtration, recrystallization, or separation by chromatography such as the improved simulated moving bed (ISMB) method.

According to a second advantageous variant of the invention, the C7 sugars, which are advantageously D-mannoheptulose and perseitol, are at least partially esterified with a —(CO)—R radical wherein R represents a saturated or unsaturated hydrocarbon chain containing from 11 to 24 carbon atoms, optionally substituted by one or more substituents selected from the group comprising hydroxy radicals (—OH), ethoxy radicals (—OC$_2$H$_5$) and an —SO$_3$M group with M representing a hydrogen atom, an ammonium ion (NH$_4^+$) or a metal ion. In particular, the C7 sugars are at least partially esterified with a fatty acid residue. The hydrocarbon chain can be linear or branched, and it is advantageously linear.

The radical R advantageously represents a fatty acid residue.

The fatty acids considered according to the invention are more particularly long-chain fatty acids, i.e., with more than 11 carbon atoms and notably more than 14 carbon atoms.

Their hydrocarbon chain can be saturated or contain one or more double bonds. As examples of these fatty acids, mention may be made notably of saturated fatty acids such as palmitic (C$_{16}$), stearic (C$_{18}$), arachidic (C$_{20}$), behenic (C$_{22}$) and lignoceric (C$_{24}$) acids and unsaturated fatty acids such as palmitoleic (C$_{16}$), oleic (C$_{18}$), linoleic (C$_{18}$), linolenic in particular in its α and γ forms (C18), and arachidonic (C$_{20}$) acids.

In particular, the radical R is advantageously selected from the group comprising stearyl, linoleyl, oleyl, palmityl, lauryl, myristyl, arachidyl, behenyl, lauroleyl, myristoleyl, palmitoleyl, linolenyl in its α and γ forms, and/or arachidonyl radicals.

It is particularly advantageous to substitute the hydrocarbon chain with an —SO$_3$M group with M representing a hydrogen atom, an ammonium ion (NH$_4^+$) or a metal ion (in particular sodium).

In derivatives of formula (I), the hydroxyl functional groups can be substituted by the residue of the same fatty acid or by residues of different fatty acids.

The C7 sugar fatty acid derivatives can be obtained by esterification reaction resulting from the bringing together, under suitable conditions, of one or more acids of formula HOOC—R (R having the same definition as in the preceding paragraphs) with commercially available (synthetic) D-mannoheptulose and/or perseitol or with the avocado sugar water-soluble extract described above.

According to a third advantageous variant of the invention, the C7 sugars, which are advantageously D-mannoheptulose and perseitol, are at least partially esterified with a —(CO)—R' radical wherein R' represents a saturated or unsaturated hydrocarbon chain containing from 2 to 10 carbon atoms, optionally substituted by one or more substituents selected from the group comprising hydroxy radicals (—OH), ethoxy radicals (—OC$_2$H$_5$) and an —SO$_3$M group with M representing a hydrogen atom, an ammonium ion (NH$_4^+$) or a metal ion. The hydrocarbon chain can be linear or branched, and it is advantageously linear.

The radical R advantageously represents a residue of a short-chain acid, i.e., with less than 10 carbon atoms and notably less than 8 carbon atoms.

Their hydrocarbon chain can be saturated or contain one or more double bonds. As an example of these acids, mention may be made notably of acetic acid.

It is particularly advantageous to substitute the hydrocarbon chain with an —SO$_3$M group with M representing a hydrogen atom, an ammonium ion (NH$_4^+$) or a metal ion (in particular sodium).

In derivatives of formula (I), the hydroxyl functional groups can be substituted by the residue of the same acid or residues of different acids.

The C7 sugar acid derivatives can be obtained by esterification reaction resulting from the bringing together, under suitable conditions, of one or more acids of formula HOOC—R' (R' having the same definition as in the preceding paragraphs) with commercially available (synthetic) D-mannoheptulose and/or perseitol or with the avocado sugar water-soluble extract described above.

According to a fourth advantageous variant of the invention, the C7 sugars, which are advantageously D-mannoheptulose and perseitol, are at least partially esterified with a —(CO)—R radical and with a —(CO)—R' radical, R and R' having the same definitions as those given in the second and third variants.

The C7 sugar acid derivatives can be obtained by esterification reaction resulting from the bringing together, under suitable conditions, of one or more acids of formula HOOC—R and one or more acids of formula HOOC—R' with commercially available (synthetic) D-mannoheptulose and/or perseitol or with the avocado sugar water-soluble extract described above.

The derivatives obtained by the second, third or fourth variants are called D-mannoheptulose acid derivative or perseitol acid derivative, respectively.

In any one of the second, third or fourth variants, the ratio between the number of ester functional groups of the compound of formula (I) and the initial number of hydroxyl functional groups, or esterification rate, for a sugar molecule, varies from 0.2 to 1. It is notably less than or equal to 0.6, and in particular less than or equal to 0.4.

The degree of esterification is controlled by reagent concentration, reaction duration and reaction temperature. It can be measured by chromatography, in particular by steric exclusion chromatography).

According to one or another of the four variants, the composition contains 0.001 to 30% by weight D-mannoheptulose or an acid derivative thereof, in relation to the total weight of said composition, and/or 0.001 to 30% by weight perseitol or an acid derivative thereof, in relation to the total weight of said composition. More particularly, the composition contains 0.002 to 5% by weight D-mannoheptulose or an acid derivative thereof, in relation to the total weight of said composition, and/or 0.002 to 5% by weight perseitol or an acid derivative thereof, in relation to the total weight of said composition.

In the context of the present invention, the composition can further contain:
- another active agent for treating alopecia; and/or
- an anti-hair loss and/or hair and nail strengthening agent; and/or
- an anti-dandruff agent.

As an agent for treating alopecia, mention can be made notably of DHEA derivatives (7-hydroxy-DHEA and 7-keto-DHEA), taurine and derivatives thereof (EP1515712), 15-hydroxyprostaglandin dehydrogenase inhibitors (such as tetrazole compounds and others described in EP1358868), retinoic acid receptor agonists (such as the compounds described in EP829256), 4-aminopiperidine derivatives (EP1849455, EP1849456), N-oxide derivatives (EP1829523), thiazolidine-2,4-dione derivatives (EP1775294, EP1739083, EP1738742), 2-thioacetamide derivatives (EP1052576), styryl-pyrazole derivatives (EP1558203), pyridine-dicarboxylic acid derivatives (EP1352629), indole carboxylic derivatives (E9964852), 2-amino-alkane-1,3-diol derivatives (EP790053), fructose, glucose and/or globular proteins of grains or hydrolysates thereof (EP648107) and pyrimidine derivatives (EP522964, EP540629, EP459890, EP420707, EP376821, EP357484, EP347328, EP336813, E2336812, EP321951, EP319027, EP304665, EP2119475; -2,4-diaminopyrimidine-3-N-oxide).

The anti-hair loss and/or hair and nail strengthening agents are advantageously phytosterols, isoflavones such as, for example, soya isoflavones, RTH16®, Aminexil®, Minoxidil®, Viviscal®, retinol, zinc and derivatives thereof, neoruscine, vitamin E, vitamin B2, vitamin B3, vitamin B6, vitamin PP, vitamin B5 (panthenol, bepanthen, dexpanthenol), vitamin B8 (vitamin H or biotin), vitamin B9 (folic acid), alpha hydroxy acid, quinine and certain sulfur-containing amino acids such as cysteine, cystine and methionone. Mention may also be made of 5-α-reductase inhibitors such as, for example, finasteride, dutasteride, *Serenoa serrulata* or *repens, Cucurbita pepo* extract or certain phytosterols. Mention may also be made of keratin, trace elements and mineral salts. Protein or lipid extracts from plants such as, for example, *Pfaffia*, sage, lemon, ginseng, quinquina, jojoba, horse chestnut, honey, wheat, nettle, echinea, cophra or coconut extracts can also be used.

The anti-dandruff agents (for the scalp) are advantageously selected from Nasturtium extract, vitamin F, thymol, clay, zinc pyrithione, zinc-PCA, zinc gluconate, zinc sulfate, camphor, myrtle extract, salicylic acid, vitamin B5, climbazole, ichthyol, selenium and derivatives thereof, squash seed extract, *Carthamus* extract, *Melaleuca* oil extract, borage and *Mimosa tenuiflora* oil, propolis, kertyol, glycolic acid, keluamid, cyclopiroxolamine, piroctone olamine, capryloyl glycine.

In the context of the present invention, the composition can further contain a dermatological active agent selected from the group comprising moisturizing active agents, keratin synthesis activators, keratoregulators, keratolytics, agents that repair the cutaneous barrier (cutaneous lipid synthesis activators or differentiation activators), healing agents, sebum-regulating agents, anti-irritant agents, soothing agents, anti-inflammatory agents, antioxidant agents, anti-aging agents, and mixtures thereof.

The most commonly used moisturizing active agents are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, polyunsaturated and monounsaturated omega-3, -6, -7 and -9 fatty acids such as linoleic acid and palmitoleic acid, sunflower oleodistillate, avocado peptides, cupuagu butter.

The keratin synthesis activators that can be used in combination are advantageously the retinoids, lupin peptides, key proteins of the stratum corneum or granulosum (keratins) and corneodesmosomes, quinoa peptides.

The most commonly used keratoregulating/keratolytic agents include: alpha-hydroxy acids (AHAs) of fruits (citric acid, glycolic acid, malic acid, lactic acid, etc.), AHA esters, combinations of AHAs with other molecules such as the combination of malic acid and almond proteins (Keratolite®), the combination of glycolic acid or lactic acid with arginine or the combination of hydroxy acid with lipid molecules such as LHA® (lipo-hydroxy acid), amphoteric hydroxy acid complexes (AHCare), willow bark (Salix alba bark extract), azelaic acid and salts and esters thereof, salicylic acid and derivatives thereof such as capryloyl salicylic acid or in combination with other molecules such as the combination of salicylic acid and polysaccharide (beta-hydroxy acid, or BHA), tazarotene, adapalene, as well as molecules of the retinoid family such as tretinoin, retinaldehyde, isotretinoin and retinol.

The healing/repairing agents that can be used in combination are advantageously vitamin A, panthenol (vitamin B5), lupeol, maca peptide extract, quinoa peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, initially found in oak gall, and catechin tannins resulting from the polymerization of flavan units whose model is provided by the catechu (*Acacia catechu*). The trace elements that can be used are advantageously selected from the group comprised of copper, magnesium, manganese, chromium, selenium, silicon, zinc and mixtures thereof. Sunflower concentrates, more advantageously linoleic sunflower concentrates may also be used, such as the active agent sold by Laboratoires Expanscience, Soline®, vegetable oil unsaponifiables such as Avocadofurane®, PPAR agonists (rosiglitazone, pioglitazone), RXR and LXR.

The sebum-regulating agents that can be used in combination are advantageously selected from the group comprising 5-α-reductase inhibitors such as, for example, the active agent 5-α Avocuta®. Zinc (and gluconate salts thereof, salicylate and pyroglutamic acid) also has sebum-suppressing activity. Mention may also be made of spironolactone, an anti-androgen and aldosterone antagonist, which significantly reduces the sebum secretion rate after 12 weeks of application. Other molecules such as, for example, *Cucurbita pepo*, extracted from pumpkin seeds, squash seed oil and palm cabbage limit sebum production by inhibiting 5-α-reductase transcription and activity. Other sebum-regulating agents of lipid origin that act on sebum quality, such as linoleic acid, are of interest.

Anti-inflammatory, anti-irritant and soothing agents limit the inflammatory reaction led via cytokines or mediators of arachidonic acid metabolism and have soothing and anti-irritant properties. The most traditional are glycyrrhetinic acid (licorice derivatives) and salts and esters thereof, lipoic acid, beta-carotene, vitamin B3 (niacinamide, nicotinamide), vitamin E, vitamin C, vitamin B12, flavonoids (green tea, quercetin, etc.), lycopene or lutein, avocado oleodistillate, arabinogalactan, lupin peptides, lupin total extract, quinoa peptide extract, Cycloceramide® (oxazoline derivative, compound called OX-100 in WO03/055463), isoflavones such as, for example, genistein/genistin, daidzein/daidzin, spring water or thermal spring water (eau d'Avène, eau de la Roche Posay, eau de Saint Gervais, eau d'Uriage, eau de Gamarde), goji (*Lycium barbarum*) extracts, plant amino acid peptides or complexes, topical dapsone, or steroidal anti-inflammatory drugs such as corticosteroids, or non-steroidal anti-inflammatory drugs (NSAIDs).

The term "antioxidant" refers to a molecule that decreases or prevents the oxidation of other chemical substances. The antioxidants that can be used in combination are advantageously selected from the group comprised of thiols and phenols, licorice derivatives such as glycyrrhetinic acid and salts and esters thereof, alpha-bisabolol, *Ginkgo biloba* extract, *Calendula* extract, Cycloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene, the large family of polyphenols such as tannins, phenolic acids, anthocyanins, flavonoids such as, for example, extracts of green tea, of red berries, of cocoa, of grapes, of *Passiflora incarnata* or of *Citrus*, or isoflavones such as, for example, genistein/genistin and daidzein/daidzin. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The anti-aging agents are advantageously antioxidants and in particular vitamin C, vitamin A, retinol, retinal, hyaluronic acid of any molecular weight, Avocadofurane®, lupin peptides and maca peptide extract.

In the context of the present invention, the composition can further contain an active agent selected from the group comprising prebiotics and probiotics, antibacterial agents, antifungal compounds, preservatives, immunomodulators, growth factors and inorganic or organic sun filters and screens (pigmentary or ultrafine).

The prebiotics and probiotics that can be used in combination are advantageously trans-galacto-oligosaccharides, fructans or fructo-oligosaccharides for prebiotics and probiotics belonging to genera *Lactobacilli* and *Bifidobacteria*.

The antifungal compounds that can be used in combination are advantageously econazole and ketoconazole.

The preservatives and antibacterial agents that can be used in combination are, for example, those generally used in cosmetics or nutraceuticals, molecules with anti-bacterial activity (pseudo-preservatives) such as caprylic derivatives like, for example, capryloyl glycine and glyceryl caprylate, such as hexanediol and sodium levulinate, zinc and copper derivatives (gluconate and PCA), phytosphingosine and derivatives thereof, benzoyl peroxide, piroctone olamine, zinc pyrithione and selenium sulfide. The antiseptic preservatives that can be used in combination are, for example, triclosan, chlorhexidine and quaternary ammonium.

The immunomodulators that can be used in combination are advantageously tacrolimus, pimecrolimus and oxazolines. The oxazolines that can be used in combination are advantageously oxazolines selected from the group comprised of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline and 2-undecyl-4-ethyl-4-hydroxymethyl-1,3-oxazoline. Even more advantageously, said oxazoline is 2-undecyl-4,4-dimethyl-1,3-oxazoline, called OX-100 or Cycloceramide®.

The growth factors that may be used in combination are advantageously becaplermin and transforming growth factor-β (TGF-β), EGF, NGF and VEGF.

As examples of sun protection active agents, mention may be made notably of titanium dioxide, zinc oxide, methylene bis-benzotriazolyl tetramethylbutylphenol (brand name: Tinosorb M) and bis-ethylhexyloxyphenol methoxyphenyl triazine (brand name: Tinosorb S), octocrylene, butyl methoxydibenzoylmethane, terephthalylidene dicamphor sulfonic acid, 4-methylbenzylidene camphor, benzophenone, ethylhexyl methoxycinnamate, ethylhexyl dimethyl PABA and diethylhexyl butamido triazone.

In the context of the present invention, the composition can further contain one or more (in particular two, three or four) active agents selected from the group comprising:
- a *Schisandra sphenanthera* fruit extract, in particular a *Schisandra sphenanthera* peptide and sugar extract;
- an avocado peptide extract, in particular that described in request WO2005/105123;
- an avocado oil (see international applications WO2004/012496, WO2004/012752, WO2004/016106, WO2007/057439);
- avocado furans, in particular Avocadofurane® (avocado furans obtained by the method described in international application WO01/21605);
- a fatty ester whose fatty chain is a linear $C_7$-$C_{30}$ hydrocarbon chain comprising between 0 and 2 ethylene unsaturations and which can be substituted by 1 to 3 hydroxy groups and/or 1 to 3 ester functional groups in addition to the principal ester functional group, in particular 5-α Avocuta® (butyl avocadate), to inhibit 5-α reductase (see WO01/52837 and WO02/06205);
- avocado and/or soya unsaponifiables, advantageously a mixture of avocado furan unsaponifiables and soya unsaponifiables, in a ratio of roughly 1:3-2:3, respectively. The avocado and soya unsaponifiables are even more advantageously the product Piascledine®, sold by Laboratoires Expanscience;
- a sunflower oleodistillate, even more advantageously with linoleic sunflower concentrates, such as the active agent sold by Laboratoires Expanscience, Soline® (see international application WO01/21150);
- lupeol (FR2822821, FR2857596);
- lupin peptides such as obtained according to the method described in application WO2005/102259;
- a total lupin extract (see international application WO2005/102259);
- a lupin oil, advantageously sweet white lupin oil, such as that described in international application WO98/47479;
- a maca peptide extract (see international application WO2004/112742);
- an oxazoline, in particular 2-undecyl-4,4-dimethyl-1,3-oxazoline (Cycloceramide®) as described in international applications WO2004050052, WO2004050079;
- rice peptides (as described in international application WO2008/009709);
- a quinoa extract, in particular a quinoa peptide extract (WO2008/080974);
- cupuaçu butter;
- a rapeseed or corn concentrate.

The composition is advantageously intended for topical or oral administration.

According to an advantageous variant, the compositions of the invention are suited to the topical administration on the scalp and include shampoos, gels, emulsions, milks, lotions, oils, aqueous or hydroalcoholic or glycolic solutions, powders, sprays or any other product for external application, such as, for example, varnishes for application on the nails.

The invention further relates to a method of cosmetic treatment of hair and nails, in particular the hair, intended to stimulate the growth thereof and/or to slow the loss thereof, characterized in that it consists in administering a cosmetic composition containing at least one derivative of formula (I) such as defined according to any of the four variants, optionally in combination with one or more of the active agents cited above.

The invention further relates to a cosmetic care method of the hair and/or eyelashes and/or nails, in order to improve the condition thereof and/or the appearance thereof, characterized in that it consists in administering a cosmetic composition containing at least one derivative of formula (I) such as defined according to any of the four variants, optionally in combination with one or more of the active agents cited above.

According to this cosmetic care method, the cosmetic composition advantageously is applied to the hair and/or eyelashes and/or nails and then left in contact with the hair and/or eyelashes and/or nails and then optionally rinsed out.

According to this cosmetic care method, the cosmetic composition is advantageously administered orally, preferably in the form of soft or hard capsules, tablets, cereal bars or beverages. The minimum and maximum daily doses are advantageously between 10 mg and 250 mg, depending on the indication: for preventive treatment, one dose one or two times/day for two months (or 10-150 mg/day) is recommended and for curative treatment, one dose two, four or six times/day for one month (or 50-250 mg/day) is recommended.

The following examples illustrate the invention but are not restrictive.

EXAMPLE 1

Preparation of an Avocado Sugar Water-Soluable Extract

Fifty kilograms of fresh avocados, the Hass variety, are cut into thin slices 2-5 mm thick, seed included, using a circular-blade slicer. The drying apparatus is a temperature controlled hot air drying oven. The sliced avocados are distributed in a thickness of 4-5 cm on stacked racks. Drying is for 48 hours at a temperature of 80° C. Once dried, the fruits are subjected to cold pressing. This operation is carried out on a small Komet® laboratory press.

Four kilograms of delipidated fruits (oil cake) are cold crushed and then extracted at reflux in the presence of 25 liters of ethanol. The fat-depleted powder is then recovered by filtration on a Büchner funnel and oven dried at 50° C. for 5 hours.

The oil cake is washed with demineralized water (10 liters) and then separated by centrifugation. The solid fraction is taken up to be purified and concentrated according to the following procedure:

Demineralization using ion exchange resins: demineralization of heptuloses by passage on OH⁻ resins and then on H⁺ resin.
Ultrafiltration at 10,000 Da: ultrafiltration is carried out with a system equipped with four membranes with a 10 kDa cut-off.
Concentration under vacuum: the purified extract is concentrated using a vacuum evaporator until a roughly 4% dry matter content is obtained.

Packaging: the concentrated extract is adjusted to 5% dry matter and preservative is added, then it is sterile filtered on a 0.2 μm cut-off membrane and packaged.

Following Table 3 gives the composition of the C7 avocado sugar extract, with 5% dry matter, prepared according to the method described above:

TABLE 3

| Appearance | Pale yellow solution |
|---|---|
| Analytic criteria | |
| Dry matter | 5% |
| pH (¼ dilution) | 7.0 |
| Absorbance at 420 nm (¼ dilution) | 0.013 |
| Absorbance at 550 nm (¼ dilution) | 0.003 |
| Composition (%/dry matter) | |
| Sucrose | 3.0 |
| Glucose | 7.5 |
| D-Mannoheptulose | 40.0 |
| Fructose | 10.6 |
| Perseitol | 28.8 |

According to this same method, two other extracts were prepared, whose pH, absorbance and C7 sugar content values are given in following Table 4. C7 sugar content corresponds to the sum of perseitol and D-mannoheptulose analyzed by HPLC.

TABLE 4

| | | Batch | |
|---|---|---|---|
| | | 1 | 2 |
| Dry matter | | 5% | 5% |
| pH (¼ dilution) | | 5.9 | 5.4 |
| Absorbance (¼ dilution) | 420 nm | 0.054 | 0.076 |
| | 550 nm | 0.004 | 0.032 |
| C7 sugars/dry matter | | 80.5 | 83.4 |

EXAMPLE 2

Evaluation of Anti-Inflammatory Properties of Avocado Sugars (Obtained in Example 1) In Vitro—Keratinocytes Stressed with LPS We evaluated the capacity to modulate the inflammatory response of the avocado sugars obtained according to Example 1, hereafter called AV119, in human primary keratinocytes stressed with LPS (lipopolysaccharide).

Methodology

The cells were pretreated with 0.1% AV119 for 24 h and successively with 10 μg/ml of LPS for 24 h. In another series of experiments, the keratinocytes were pretreated with 30 μM calpain and successively with 10 μg/ml LPS for 24 h. Calpain is a specific inhibitor of the transcription factor NFκB, a key element of the inflammatory cascade. A control of keratinocytes treated only with AV119 was prepared.

Expression of mRNA for the cytokines IL-6, IL-8, IL-1α and TNF-α was analyzed by real-time PCR and protein production and release were analyzed by ELISA in the culture supernatants. Moreover, ICAM-1 expression and production were also analyzed. Finally, IκB phosphorylation was analyzed to measure the activation of transcription factor NFκB.

Real-Time PCR:

Total RNA was extracted with the High Pure RNA Isolation Kit (Roche Diagnostics) according to the manufacturer's recommendations. 1 ng of RNA was reverse-transcribed into complementary DNA (cDNA) (Expand Reverse Transcriptase, Roche Diagnostics) using hexamer primers (random hexamers, Roche Diagnostics), at 42° C. for 45 min, according to the manufacturer's instructions. Real-time PCR was carried out using SYBR Green technology with the LC Fast Start DNA Master SYBR Green kit (Roche Diagnostics) (LightCycler 2.0 Instrument). The melting curve was analyzed at the end of each amplification to ensure the absence of non-specific reaction products. Quantification rests on the measure of threshold cycles (CT), which are measured at the beginning of the exponential phase of the reaction and on the normalization of the internal standard curve obtained with the reference gene beta-actin.

ELISA Test for IL-6, IL-8, IL-1α, TNF-α and ICAM-1:

A standard protocol was used for the ELISA tests (Phoenix Pharmaceuticals, Inc.).

Western Blot:

Proteins were extracted from the keratinocytes by cold homogenization in lysis buffer (50 mM HEPES pH 7.5, 150 mM NaCl, 1% glycerol, 1% Triton, 1.5 mM $MgCl_2$, 5 mM EGTA) supplemented with 20 mM sodium pyrophosphate, 10 mM sodium orthovanadate and 25 mM NaF and protease inhibitors (aprotinin, phenylmethanesulfonyl fluoride (PMSF)). Protein level was quantified by the Bradford method. 5 μg of protein was deposited on a 12.5% or 7% polyacrylamide electrophoresis gel and was transferred on nitrocellulose membranes. The membranes were saturated overnight with 5% nonfat milk and then incubated with 1 μg/ml anti-IκB-α polyclonal antibody (Santa Cruz) overnight at 4° C., or with 1 μg/ml anti-phospho-IκB-α monoclonal antibody (Stressgen, Milan, Italy) for 2 h at room temperature. After rinsing, the membranes were developed by the peroxidase/chemiluminescence system (ECL System, Amersham Biosciences Biotech, Milan, Italy).

Results

TABLE 5

Gene expression (mRNA, real-time PCR) of pro-inflammatory cytokines IL-6, IL-8, IL-1α and TNF-α in keratinocytes stresses with LPS and treated with AV119

|  | IL-6 | IL-8 | IL-1α | TNF-α |
| --- | --- | --- | --- | --- |
| 0.1% AV119 | 3.0 | 1.5 | 2.0 | 1.9 |
| LPS | 54.5 | 54.1 | 71.5 | 68.0 |
| LPS + 0.1% AV119 | 15.3 | 10.0 | 7.2 | 17.7 |
| LPS + calpain 1 | 5.0 | 5.0 | 6.0 | 6.5 |

TABLE 6

Protein production (ELISA) of pro-inflammatory cytokines IL-6, IL-8, IL-1α and TNF-α in keratinocytes stressed with LPS and treated with AV119

|  | IL-6 | IL-8 | IL-1α | TNF-α |
| --- | --- | --- | --- | --- |
| Control | 2 | 1.5 | 2.5 | 1.9 |
| 0.1% AV119 | 4 | 3.5 | 3 | 2.8 |
| LPS | 76 | 85 | 82 | 96.0 |
| LPS + 0.1% AV119 | 13 | 10 | 11 | 17.7 |
| LPS + calpain 1 | 9 | 8 | 5 | 6.5 |

TABLE 7

Gene expression (mRNA, real-time PCR) of adhesion molecule ICAM-1 in keratinocytes stressed with LPS and treated with AV119

|  | ICAM-1 |
| --- | --- |
| 1% AV119 | 1.0 |
| LPS | 53.2 |
| LPS + 1% AV119 | 20.7 |
| LPS + calpain 1 | 7.0 |

TABLE 8

Protein production (ELISA) of adhesion molecule ICAM-1 in keratinocytes stressed with LPS and treated with AV119

|  | ICAM-1 |
| --- | --- |
| Control | 2.0 |
| 1% AV119 | 4.0 |
| LPS | 85 |
| LPS + 1% AV119 | 34.0 |
| LPS + calpain 1 | 7.0 |

The transcription factor NFκB is in inactive form in the cell cytoplasm when the IκB subunit contained within it is dephosphorylated. Thus, IκB phosphorylation activates the factor NFκB. Activated NFκB is then translocated into the nucleus where it interacts with the specific sequences of the genes it regulates and thus activates their transcription. NFκB regulates many inflammation genes.

In the experiment, LPS strongly induced IκB phosphorylation and thus activation of transcription factor NFκB, whereas AV119 inhibits IκB phosphorylation quite clearly and with the same intensity as the NFκB inhibitor, calpain. The avocado sugars AV119, in this experiment, demonstrate their capacity to inhibit the transcription factor NFκB.

Conclusion

The results clearly show that the avocado sugars AV119 are capable of inhibiting the inflammatory response induced by LPS in the same way as the NFκB inhibitor (calpain) by decreasing cytokines IL-6, IL-8, IL-1α and TNF-α on the mRNA (Table 5) and protein (Table 6) levels. In addition, the sugars AV119 are also capable of inhibiting the adhesion molecule ICAM-1 on the mRNA (Table 7) and protein (Table 8) levels.

Moreover, the results show that LPS is capable of inducing IκB activation by phosphorylating it whereas avocado sugars, just as the specific NFκB inhibitor (calpain), are capable of inhibiting IκB phosphorylation and thus its activation (Figure 1). Thus, by limiting IκB activation, avocado sugars limit activation of the transcription factor NFκB and thus inhibit activation of the inflammatory response.

EXAMPLE 3

Evaluation of Anti-Inflammatory Properties of Avocado Sugars (Obtained in Example 1) In Vitro—Keratinocytes Stressed with PMA We evaluated the capacity to modulate the inflammatory response of the avocado sugars obtained according to Example 1, hereafter called AV119, in human primary keratinocytes stressed with PMA (phorbol myristic acetate).

Methodology

At day 0 (D0), normal human epidermal keratinocytes (NHEK) are seeded in hydrocortisone-free KGM2 medium.

At subconfluence (at D1), the NHEK are rinsed with PBS and then pretreated with 0.005% and 0.05% avocado sugars AV119 or 0.1 µM dexamethasone (positive control) (Sigma, product D4902) in hydrocortisone-free KGM2 medium.

Twenty-four hours later, the NHEK are treated overnight with 10 µg/ml PMA (phorbol myristate acetate).

After incubation, the culture supernatants are collected and stored at −80° C. awaiting the cytokine (IL-1β, TNF-α, IL-8) ELISA (R&D Systems kits).

In parallel, the number of living cells is determined by a neutral red test.

The quantity of cytokine assayed for each condition (concentration in pg/ml, or $OD_{450}$) is reduced to the number of living cells by dividing by the $OD_{540}$ value obtained at the end of the neutral red test.

The results are compared statistically using a one way ANOVA followed by a Tukey's test.

Results

TABLE 9

Analysis of IL-1β release by keratinocytes stressed with PMA and treated with AV119

| Conditions | IL-1β pg/ml/$OD_{450}$ (mean ± SD) | Significance | % in relation to the control |
|---|---|---|---|
| Control without PMA | 0.729 ± 0.440 | | |
| PMA | 10.930 ± 0.190 | $$$ | 1399 |
| Dexamethasone | 3.232 ± 0.329 | *** | −70 |
| 0.005% AV119 | 4.163 ± 0.723 | *** | −62 |
| 0.05% AV119 | 3.169 ± 1.141 | *** | −71 |

$$$ $p < 0.001$: increase by PMA in relation to the untreated control (without PMA)
*** $p < 0.001$: inhibition by dexamethasone or AV119 in relation to PMA

TABLE 10

Analysis of TNF-α release keratinocytes stressed with PMA and treated with AV119

| Conditions | TNF-α pg/ml/$OD_{450}$ (mean ± SD) | Significance | % in relation to the control |
|---|---|---|---|
| Control without PMA | 0.049 ± 0.006 | | |
| PMA | 0.584 ± 0.079 | $$$ | 1091 |
| Dexamethasone | 0.328 ± 0.007 | | −44 |
| 0.005% AV119 | 0.311 ± 0.019 | * | −47 |
| 0.05% AV119 | 0.385 ± 0.059 | | −34 |

$$$ $p < 0.001$: increase by PMA in relation to the untreated control (without PMA)
* $p < 0.01$: inhibition by dexamethasone or AV119 in relation to PMA

TABLE 11

Analysis of IL-8 release by keratinocytes stressed with PMA and treated with AV119

| Conditions | IL-8 pg/ml/$OD_{450}$ (mean ± SD) | Significance | % in relation to the control |
|---|---|---|---|
| Control without PMA | 0.158 ± 0.064 | | |
| PMA | 1.765 ± 0.305 | $$$ | 1017 |
| Dexamethasone | 0.790 ± 0.089 | *** | −55 |
| 0.005% AV119 | 0.739 ± 0.037 | *** | −58 |
| 0.05% AV119 | 0.792 ± 0.170 | *** | −55 |

$$$ $p < 0.001$: increase by PMA in relation to the untreated control (without PMA)
*** $p < 0.001$: inhibition by dexamethasone or AV119 in relation to PMA Conclusion In this study, we demonstrated that PMA significantly induced primary mediators of inflammation (IL-1β, TNF-α) as well as the secondary mediator, the chemokine IL-8. We clearly demonstrated that the avocado sugars AV119 inhibit pro-inflammatory mediators strongly and in a manner comparable to dexamethasone, which known for its anti-inflammatory properties.

EXAMPLE 4

Examples of Formulations Topical Application

Keratinizing Fluid

| Raw material/brand name | % |
|---|---|
| Cetyl alcohol | 1-5% |
| Silicone 345 | 1-5% |
| Antioxidant | 0-1% |
| Purified water | qsp 100% |
| Cetrimonium chloride | 0-5% |
| Avocado sugars (Example 1) | 0-5% |
| Maca peptide extract | 0-5% |
| Hydrolyzed wheat protein | 0-1% |
| Preservative | 0-2% |
| Fragrance | 0-1% |
| pH adjuster | 0-1% |

Regulating Shampoo

| Raw material/brand name | % |
|---|---|
| Purified water | qsp 100% |
| Lauroamphoacetate | 5-20% |
| Cocoglucoside | 5-20% |
| PEG 6000 distearate | 1-5% |
| Preservatives | 0-2% |
| Esterified avocado sugars (Example 2) | 0-5% |
| Cycloceramides | 0-5% |
| Zinc pyrithione | 0-1% |
| pH adjuster | 0-1% |
| Sequestrant | 0-1% |
| Fragrance | 0-1% |

Antidandruff Shampoo

| Raw material/brand name | % |
|---|---|
| Purified water | qsp 100% |
| Lauroamphoacetate | 5-20% |
| Cocoglucoside | 5-20% |
| PEG 6000 distearate | 1-5% |

-continued

| Raw material/brand name | % |
|---|---|
| Preservatives | 0-2% |
| Avocado sugars (Example 1) | 0-5% |
| Sunflower oleodistillate | 0-5% |
| pH adjuster | 0-1% |
| Sequestrant | 0-1% |
| Fragrance | 0-1% |

Conditioner

| Raw material/brand name | % |
|---|---|
| Cetearyl alcohol/ceteareth-33 | 1-5% |
| Quaternium-82 | 0-2% |
| Purified water | qsp 100% |
| Hydrolyzed wheat protein | 0-5% |
| Preservatives | 0-2% |
| pH adjuster | 0-1% |
| Fragrance | 0-1% |
| Lupin total extract | 0-5% |
| Esterified avocado sugars (Example 2) | 0-5% |

Capillary Lotion

| Raw material/brand name | % |
|---|---|
| Purified water | qsp 100% |
| Methyl propanediol | 5-20% |
| Preservative | 0-2% |
| pH adjuster | 0-1% |
| Fragrance | 0-1% |
| Avocado sugars (Example 1) | 0-5% |
| Lupeol | 0-5% |
| Ethylhexyl cocoate | 0-5% |
| PEG-40 castor oil | 0-5% |

Hairspray

| Raw material/brand name | % |
|---|---|
| Purified water | qsp 100% |
| Sodium magnesium silicate | 1-5% |
| Ethanol | 5-20% |
| pH adjuster | 0-1% |
| Fragrance | 0-1% |
| Avocado sugars (Example 1) | 0-5% |
| PVP | 0-5% |
| PEG-40 castor oil | 0-5% |

Hair Gel

| Raw material/brand name | % |
|---|---|
| Purified water | qsp 100% |
| Carbomer | 0-5% |
| Silicone | 0-10% |
| pH adjuster | 0-2% |
| Fragrance | 0-1% |
| Avocado sugars (Example 1) | 0-5% |
| Hydrolyzed wheat protein | 0-5% |
| PEG-40 castor oil | 0-5% |

Styling Gel

| Raw material/brand name | % |
|---|---|
| Purified water | qsp 100% |
| Carbomer | 0-5% |
| AMP-acrylates/allyl methacrylate copolymer | 0-10% |
| pH adjuster | 0-2% |
| Fragrance | 0-1% |
| Avocado sugars (Example 1) | 0-5% |
| PEG-40 castor oil | 0-5% |

Varnish for Fragile and Brittle Nails

| Raw material/brand name | % |
|---|---|
| Acrylate copolymer | 15-30% |
| Ethanol | qsp 100% |
| Acetone | 5-20% |
| Avocado sugars (Example 1) | 0-5% |

EXAMPLE 5

Examples of Formulations—Compositions for Oral Administration

1) Anti-Hair Loss Composition in the Form of Soft Capsules
A-Composition 1

| | |
|---|---|
| Avocado sugars (Example 1) | 30 mg |
| Squash seed oil | 100 mg |
| Methionine | 100 mg |
| Vitamin of group B (B1, B2, B3, B5, B6, B9, B12) | qsp 100% RDA |
| Zn chelate | qsp 100% RDA |
| Fe chelate | qsp 100% RDA |
| Beeswax | |
| Soya lecithin | |
| Alimentary gelatin | |
| Glycerin | |

This composition is administered as two 500 mg capsules per day.

B-Composition 2

| | |
|---|---|
| Avocado sugars (Example 2) | 40 mg |
| Cereal oil rich in ceramides and polar lipids | 300 mg |
| Lupin oil | 50 mg |
| Vitamin E | qsp 100% RDA |
| Vitamin C | qsp 50% RDA |
| Beeswax | |
| Soya lecithin | |
| Alimentary gelatin | |
| Glycerin | |

This composition is administered as four to six 500 mg capsules per day.

2) Hair Fortifying Tablets

| | |
|---|---|
| Avocado sugars (Example 1) | 40 mg |
| Cereal extracts (corn, buckwheat, millet, spelt) rich in sulfur-containing amino acids | 200 mg |
| Vitamin C | qsp 100% RDA |
| Fish cartilage glycosaminoglycans | 200 mg |
| Glucidex IT 19 (compression agent) | qsp one 800 mg tablet |

This composition is administered as two to six tablets per day.

3) Nail Fortifying Formula

| | |
|---|---|
| Avocado sugars (Example 1) | 150 mg |
| Cereal extracts (corn, buckwheat, millet, spelt) rich in sulfur amino acids | 200 mg |
| Zn in chelate form | |
| Bamboo extract rich in silicic acid | 100 mg |
| Fish cartilage glycosaminoglycans | 200 mg |
| Fruit flavor (citrus fruits, red berries), potassium acesulfame, Glucidex IT 19 (compression agent) | qsp one 2000 mg tablet |

This composition is administered once per day.

4) Anti-Hair Loss Powder Stick

| | |
|---|---|
| Avocado sugars (Example 1) | 100 mg |
| Polyphenol-rich tea extract | 100 mg |
| OPC-rich grape extract | 50 mg |
| Hop extract rich in 8-prenylnaringenin | 50 mg |
| Xanthan gum | |
| Sodium ascorbate | |
| Maltodextrin | |

Said composition is administered twice per day.

5) Chocolate-Flavored Nail-Strengthening Cereal Bar

| | |
|---|---|
| Avocado sugars (Example 1) | 150 mg |
| Glycosaminoglycans | 100 mg |
| Hyaluronic acid | 500 mg |
| Horsetail extract rich in silicic acid | 100 mg |
| Natural tocopherols | 4 mg |
| Dark chocolate, oligofructose, sugar, fructose syrup, fat-reduced cocoa, crunchy cereals, powdered skim milk, almonds, glycerol, sorbitol, vegetable oils, glucose syrup, flavoring, sweetened condensed milk, soya lecithin, fatty acid mono- and diglycerides, caramelized syrup, maltodextrin, salt, potassium sorbate, alpha-tocopherol | qsp one 50 g bar |

This composition is administered once per day.

6) Vanilla-Flavored Anti-Hair Loss Cereal Bar

| | |
|---|---|
| Esterified avocado sugars (Example 2) | 150 mg |
| Cereal extracts (corn, buckwheat, millet, spelt) rich in sulfur-containing amino acids | 200 mg |
| Fish cartilage glycosaminoglycans | 500 mg |
| Protein hydrolysate rich in type-II collagen | 500 mg |
| Polyphenol-rich green tea extract | 200 mg |
| Oligofructose, sugar, fructose syrup, crunchy cereals, powdered skim milk, almonds, glycerol, sorbitol, vegetable oils, glucose syrup, flavoring, sweetened condensed milk, soya lecithin, fatty acid mono- and diglycerides, caramelized syrup, maltodextrin, salt, potassium sorbate, alpha-tocopherol | qsp one 50 g bar |

This composition is administered once per day.

7) Hard Nails Praline-Flavored Lacteal Beverage

| | |
|---|---|
| Avocado sugars (Example 1) | 150 mg |
| Polyphenol-rich green tea extract | 100 mg |
| Vitamin of group B (B1, B2, B3, B5, B6, B9, B12) | qsp 100% RDA |
| Zn, Mg, Se | qsp 100% RDA |
| Hyaluronic acid | 200 mg |
| Bamboo extract rich in silicic acid | 200 mg |
| Skimmed milk powder, flavoring, fructose, egg white, hazel nuts, sugar, caramel, beta-carotene, xanthan gum, aspartame, potassium acesulfame, soya lecithin, maltodextrin | |

This composition is administered once per day.

The invention claimed is:

1. A method to stimulate the growth of hair and/or to slow the loss of the hair, comprising administering to a person suffering from alopecia a composition comprising a mannoheptulose, a perseitol, or a mixture thereof and an acceptable excipient, wherein the source of mannoheptulose and perseitol is completely delipidated avocado fruit.

2. The method of claim 1, wherein the composition is topically applied to the hair and/or eyelashes and then left in contact with the hair and/or eyelashes.

3. The method of claim 1, wherein the composition is topically applied to the hair and/or eyelashes and then left in contact with the hair and/or eyelashes and rinsed.

4. The method of claim 1, wherein the composition is administered orally.

5. The method of claim 4, wherein the composition is administered in the form of soft or hard capsules, tablets, cereal bars or beverages.

6. The method of claim 1, wherein said composition contains 0.001 to 30% by weight D-mannoheptulose, in relation to the total weight of said composition, and/or 0.001 to 30% by weight perseitol, in relation to the total weight of said composition.

7. The method of claim 6, wherein the source of D-mannoheptulose and/or perseitol is an avocado sugar water-soluble extract.

8. The method of claim 7, wherein the avocado sugar water-soluble extract is obtained by a method comprising the following successive steps:
   an avocado oil cake is obtained through drying and extraction of the lipids; after which
   grinding and extraction with water or with hydroalcoholic mixture of said oil cake, then decanting and centrifugation in order to recover a soluble fraction rich in C7 sugars (elimination of the cake);
   demineralization on ionic resin of said soluble fraction obtained in the preceding step; then
   ultrafiltration at 10,000 daltons; and
   concentration under vacuum
   and packaging.

9. The method of claim 8, wherein the avocado oil cake is obtained from avocado fruit.

10. The method of claim 9, wherein the avocado sugar water-soluble extract contains by weight in relation to the total weight of the dry matter of the extract (relative composition determined by HPLC):
    D-Mannoheptulose 5-80%
    Perseitol 5-80%
    Sucrose less than 10%
    Glucose less than 10%, and
    Fructose less than 10%.

11. The method of claim 1, wherein said composition further contains another active agent for treating alopecia, and/or an anti-hair loss and/or hair and nail strengthening agent, and/or an anti-dandruff agent.

12. The method of claim 11, wherein said composition further contains a dermatological active agent selected from the group comprising moisturizing active agents, keratin synthesis activators, keratoregulators, keratolytics, agents that repair the cutaneous barrier, healing agents, sebum-regulating agents, anti-irritant agents, soothing agents, anti-inflammatory agents, antioxidant agents, anti-aging agents, and mixtures thereof.

13. The method of claim 11, wherein said composition further contains an active agent selected from the group comprising prebiotics and probiotics, antibacterial agents, antifungal compounds, preservatives, immunomodulators, growth factors and inorganic or organic sun filters and screens (pigmentary or ultrafine).

14. The method of claim 11, wherein said composition further contains an active agent selected from the group comprising:
- a *Schisandra sphenanthera* fruit extract;
- an avocado peptide extract;
- an avocado oil;
- avocado furans;
- a fatty ester whose fatty chain is a linear $C_7$-$C_{30}$ hydrocarbon chain comprising between 0 and 2 ethylene unsaturations and which can be substituted by 1 to 3 hydroxy groups and/or 1 to 3 ester functional groups in addition to the principal ester functional group;
- avocado and/or soya unsaponifiables;
- a sunflower oleodistillate;
- lupeol;
- lupin peptides;
- a total lupin extract;
- a lupin oil;
- a maca peptide extract;
- an oxazoline;
- a *quinoa* extract;
- rice peptides;
- cupuaçu butter; and
- a rapeseed or corn concentrate.

15. The method of claim 14, wherein the *Schisandra sphenanthera* is a *Schisandra sphenanthera* peptide and sugar extract.

16. The method of claim 14, wherein the fatty ester is butyl avocadate.

17. The method of claim 14, wherein the oxazoline is 2-undecyl-4,4-dimethyl-1,3-oxazoline.

18. The method of claim 14, wherein the *quinoa* extract is a *quinoa* peptide extract.

* * * * *